July 15, 1958 H. M. TIRET Plant Pat. 1,731
FUCHSIA PLANT
Filed Oct. 21, 1957
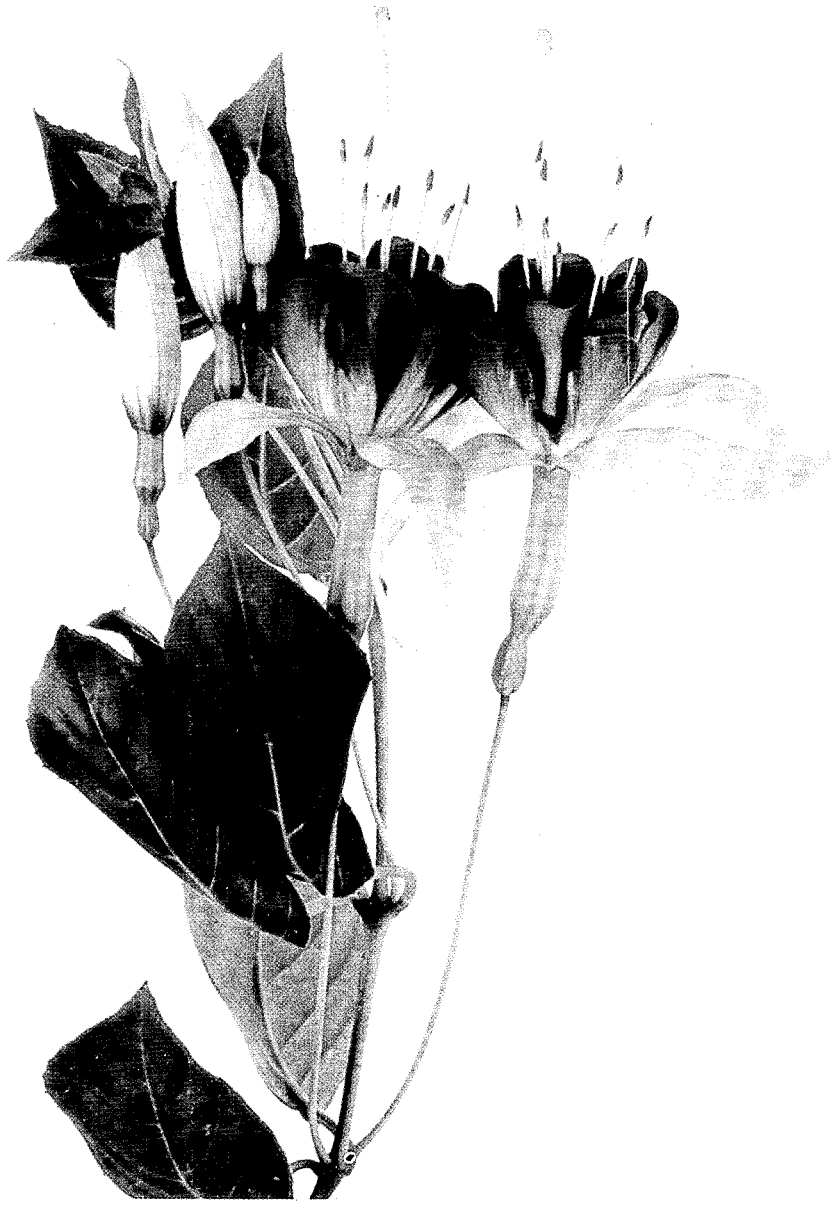

United States Patent Office

Plant Pat. 1,731
Patented July 15, 1958

1,731

FUCHSIA PLANT

Horace M. Tiret, San Francisco, Calif.

Application October 21, 1957, Serial No. 691,523

1 Claim. (Cl. 47—60)

This invention relates to a new and improved fuchsia plant, the principal new and different characteristic of which is the contrasting color and the exceptional trailing habit of growth.

As a hybrid from a seedling (unpatented) not introduced to the trade, namely 7–57–24, and San Francisco (unpatented), the figures representing applicant's own breeding symbols; the plant has been asexually reproduced at Colma, California, and Gardena, California, by cuttings which retained the characteristics of the parent fuchsia.

The plant is a trailing variety of vigorous growth. It blooms early, and produces large quantities of blooms on long stems over a lengthy blooming season.

In the accompanying drawing, the figure shows a typical branch tip; the drawing represents approximate actual size.

A detailed description of this new variety of fuchsia plant follows:

*Habit of growth.*—Vigorous growth, with exceptional traling characteristics, and unusually long blooming season.

*Foliage.*—Medium large in size, dark bright green in color. Leaves are smoothly veined with serrated edges. The branches are also green with a rosy cast. The mature leaf is approximately 3¾″ in length and 2¼″ in width at the widest point.

*Petals.*—The petals are uniformly Vermilion (British Horticultural Chart #18/2) at the base, spreading to China Rose (British Horticultural Chart #024) in the outer area toward the tips. The petals vary in intensity of Vermilion and China Rose and the outer petals contain distinct Vermilion mottling effects.

The petals number approximately 18. They are formed close together, one on top of the other, giving the corolla a somewhat stream-lined effect. As the flower matures, the petals open slightly from the formation described. The diameter of the mature flower is approximately 2″, with the length of the large petals approximately 1¾″ and the width of such petals, spread out, is approximately 1½″. The petals are smooth in appearance.

*Ovary.*—Light, bright green with brownish red strips. Length approximately ½″, width at widest point approximately ¼″, when the flower is fully open.

*Tube.*—Extremely long and slender. Length approximately 1⅝″, width at widest point approximately ⅜″. The color is Neyron Rose (British Horticultural Chart #623/3) striped with Neyron Rose (British Horticultural Chart #623).

*Sepals.*—The sepals are colored underside Neyron Rose (British Horticultural Chart #623/3) deepening in color toward the tip to Neyron Rose (British Horticultural Chart #623/1). The topside of the sepals is Neyron Rose (British Horticultural Chart #623) at the base, lightening to Neyron Rose (British Horticultural Chart #623/3) toward the tip. They are medium slender in form and curved horizontally when the flower is fully mature. The under side has a smooth crepe-like appearance, while the other side is smooth in appearance. The sepals are four in number and measure 2¾″ in length, and ¾″ in width at the widest point.

*Stamens.*—Eight in number. The stamens are flesh colored, as are the anthers, the latter being striped dark rose.

*Pistil.*—The style is colored pale carmine, and the stigma creamy white. The style is approximately 5¼″ in length measuring from the tip of the ovary, and approximately 1/32″ in width.

*Buds.*—Long and slender, being approximately 3″ in length measured from the ovary, and ¾″ in width measured at the widest point.

*Parentage.*—Applicant's own seedling (unpatented) not introduced to the trade, applicant's breeding symbol 7–57–24, and San Francisco (unpatented).

Having thus disclosed my discovery, I claim:

A new and distinct variety of fuchsia plant herein described, and as set forth in the accompanying drawing, characterized by the exceptional trailing habit of growth in combination with the extra long stems and buds, which open up to reveal a flower of long sepals and a corolla of unusual color, as herein described, resulting in an appearance unlike any fuchsia plant of its type.

No references cited.